(12) United States Patent
Schmitz et al.

(10) Patent No.: US 9,463,889 B2
(45) Date of Patent: Oct. 11, 2016

(54) PREFILLED RESERVOIR APPARATUS FOR AMBULATORY INFUSION DEVICE

(71) Applicant: MEDTRONIC, INC., Minneapolis, MN (US)

(72) Inventors: Michael C. Schmitz, Prior Lake, MN (US); Dale F. Seeley, Spring Park, MN (US); Keith R. Hildebrand, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 145 days.

(21) Appl. No.: 14/063,883

(22) Filed: Oct. 25, 2013

(65) Prior Publication Data

US 2015/0119821 A1    Apr. 30, 2015

(51) Int. Cl.
| | |
|---|---|
| *B65B 55/12* | (2006.01) |
| *B65B 3/04* | (2006.01) |
| *B65B 3/00* | (2006.01) |
| *A61M 5/142* | (2006.01) |

(52) U.S. Cl.
CPC .......... *B65B 55/12* (2013.01); *A61M 5/14248* (2013.01); *B65B 3/003* (2013.01); *B65B 3/04* (2013.01); *A61M 2005/14268* (2013.01); *A61M 2205/6045* (2013.01); *A61M 2209/045* (2013.01)

(58) Field of Classification Search
CPC ............ A61M 5/14248; A61M 2005/14268; A61M 5/1413; A61M 5/14244; A61M 2005/14252; A61M 5/162; A61M 5/172; A61M 5/16804; A61M 5/14; B65B 55/12; B65B 3/04

USPC ............ 604/131, 132, 151, 152, 890.1, 246, 604/141

See application file for complete search history.

(56) References Cited

U.S. PATENT DOCUMENTS

| | | | | |
|---|---|---|---|---|
| 5,330,431 | A | * | 7/1994 | Herskowitz .................. 604/153 |
| 5,921,962 | A | * | 7/1999 | Kriesel et al. ................ 604/132 |
| 5,928,205 | A | * | 7/1999 | Marshall ...................... 604/263 |
| 7,303,543 | B1 | | 12/2007 | Maule |
| 7,713,240 | B2 | | 5/2010 | Istoc |
| 2007/0048360 | A1 | * | 3/2007 | R. Carrara ........... A61K 9/0014 424/443 |
| 2007/0059365 | A1 | * | 3/2007 | Pollock et al. ............... 424/468 |
| 2008/0004329 | A1 | * | 1/2008 | Jamieson ............ A61K 9/0014 514/418 |
| 2008/0319393 | A1 | * | 12/2008 | Elder ............................ 604/151 |
| 2010/0121306 | A1 | * | 5/2010 | Yodfat et al. ................ 604/500 |
| 2011/0054285 | A1 | | 3/2011 | Searle |
| 2012/0053522 | A1 | | 3/2012 | Yodfat |

\* cited by examiner

*Primary Examiner* — Imani Hayman
*Assistant Examiner* — Hamza Darb
(74) *Attorney, Agent, or Firm* — Mueting, Raasch & Gebhardt, P.A.

(57) ABSTRACT

Prefilled reservoir apparatuses for use in ambulatory infusion devices include a rigid top and a flexible bag that forms at least a portion of a reservoir containing a liquid medicament composition. The reservoir apparatuses include a septum assembly that includes a fluid flow path in communication with the reservoir and a self-sealing septum disposed in or over the fluid flow path. The septum is positioned and configured to be pierced by a cannula of a base of an infusion device when the reservoir apparatus is received by the base.

20 Claims, 6 Drawing Sheets

US 9,463,889 B2

PREFILLED RESERVOIR APPARATUS FOR AMBULATORY INFUSION DEVICE

FIELD

This disclosure generally relates to, among other things, medical infusion devices and reservoirs thereof.

BACKGROUND

For most ambulatory infusion devices, reservoir size, shape and interface points are unique to the specific device because the medical device manufacture industry has not yet developed standards in this regard. Therefore, methods for filling reservoirs of an ambulatory infusion device are unique to the specific device. Reservoir filling methods often require the drug to be transferred safely from a standardized storage container (e.g., vial, syringe, ampule, etc.) to the custom device reservoir. Such techniques may be difficult for potential ambulatory infusion device users because of their lack of aptitude or understanding of medical devices and health care practice. Furthermore, some ambulatory infusion device users have cognitive or motor skill deficiencies or fear of needles that make it difficult to perform filling procedures. While the refill process can be performed by a caregiver, pharmacist, or clinician, the process still remains tedious and can be inconvenient, particularly in situations where refilling occurs every few days or less.

SUMMARY

This disclosure describes, among other things, a prefilled reservoir apparatus housing a liquid medicament composition. A reservoir may be filled by a device manufacturer, a drug manufacturer, a contract manufacturer, a pharmacist, a health care professional, or the like. The prefilled reservoir apparatus is preferably filled under conditions that ensure sterility or are terminally sterilized with the drug product prior to delivery to a patient. Preferably, the reservoir apparatus is capable of being handled and incorporated into an infusion system by a variety of patients, including patients suffering from cognitive or movement disorders.

In embodiments described herein, a prefilled reservoir apparatus for a medical infusion device includes a rigid top having an upper surface and an opposing lower surface. The top is configured to be received by a base of a medical infusion apparatus. The reservoir apparatus further includes a flexible bag forming at least a portion of the reservoir. The bag is attached to the lower surface of the rigid top. The prefilled reservoir apparatus also includes a liquid composition comprising a medicament. The liquid composition is disposed within the reservoir. The reservoir apparatus additionally includes a septum assembly comprising a fluid flow path in communication with the reservoir and a self-sealing septum disposed in or over the flow path. The septum is positioned and configured to be pierced by a non-coring cannula of the base when the top is received by the base. The septum is configured to seal about the cannula to prevent flow of the liquid composition from the reservoir through the septum around the cannula and to allow flow of the liquid composition from the reservoir to a lumen of the cannula.

In embodiments described herein, a prefilled reservoir apparatus for a medical infusion device includes (i) a rigid housing configured to be received by a base of a medical infusion apparatus, (ii) a flexible bag forming a reservoir and disposed in the housing, (iii) a liquid composition comprising a medicament and disposed within the reservoir; and (iv) a septum assembly comprising a fluid flow path in communication with the reservoir and a self-sealing septum disposed in or over the fluid flow path. The septum is positioned and configured to be pierced by a non-coring cannula of the base when the housing is received by the base. The septum is configured to seal about the cannula to prevent flow of the liquid composition from the reservoir through the septum around the cannula and to allow flow of the liquid composition from the reservoir to a lumen of the cannula.

In embodiments, methods for filling the reservoir apparatuses are described herein. For example, a method may include filling a reservoir of a reservoir apparatus with liquid composition comprising a medicament and sterilizing the liquid composition within the reservoir. The reservoir apparatus is configured to be incorporated into a medical infusion apparatus and is formed, at least in part, by a flexible bag. In embodiments, the reservoir apparatus is a reservoir apparatus described herein. In embodiments, the reservoir apparatus has one or more alignment features and a septum assembly, and the method further includes aligning the one or more alignment features with complementary features of a reservoir filling apparatus. Filling the reservoir includes inserting a non-coring cannula of the filling apparatus through a septum of the septum assembly.

One or more embodiments of the devices, systems or methods described herein provide one or more advantages over prior devices, systems or methods. As indicated above, the methods, devices and systems described herein preferably allows a patient or healthcare provider to more easily and reliably provide therapy via ambulatory infusion devices. The prefillable reservoirs and associated devices, systems and methods described herein may, in various embodiments, provide a suitable solution to the difficulties patients with movement disorders currently have with filling reservoirs. These and other advantages will be readily understood from the following detailed description.

Figure 1:
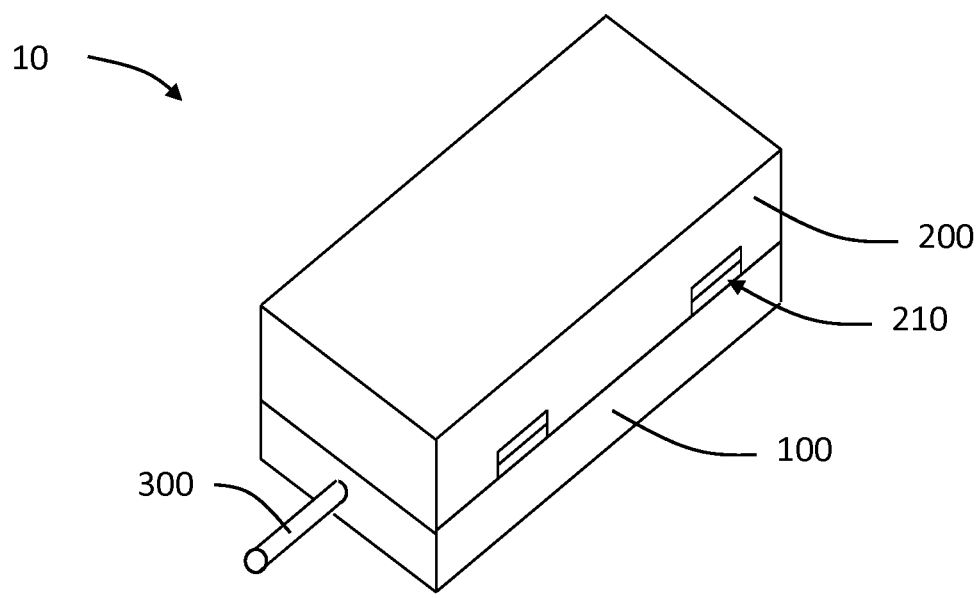
FIGS. 1-2 are schematic perspective views of embodiments of ambulatory infusion devices.

The schematic drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description several specific embodiments of compounds, compositions, apparatuses, systems and methods are disclosed. It is to be understood that other embodiments are contemplated and may be made without departing from the scope or spirit of the present disclosure. The following detailed description, therefore, is not to be taken in a limiting sense.

This disclosure generally relates to, inter alia, prefilled reservoir apparatuses and associated infusion devices, systems and methods. The prefilled reservoir apparatuses may be in the form of pods, bags, discs, cartridges or the like. Preferably, the reservoir apparatuses are easily handled, manipulated, and capable of being inserted in or removed from an associated infusion device or system, such as ambulatory infusion devices, by patients. Preferably, the reservoir apparatuses are capable of being handled and operated by patients suffering from movement disorders or having limited dexterity. Regardless of the disease from which the patient is suffering, the prefilled reservoir apparatuses described herein may allow the patient to reduce visits to a healthcare professional due to, among other things, the patient's ability to readily replace the reservoir apparatuses.

The prefillable reservoirs described herein may be employed by any suitable ambulatory infusion device. As used herein, "ambulatory", with regard to an infusion device, means that the infusion device is wearable or attachable to a patient such that the patient can readily move about while wearing the device or while the device is attached to the patient. Ambulatory pumps may be configured to deliver medicaments transdermally, transcutaneously, subcutaneously, or the like. Ambulatory pumps include patch pumps that are configured to adhere to a patient's skin. Examples of ambulatory pumps include Medtronic MiniMed's PARADIGM insulin pumps, Animas Corporation's VIBE and ONE TOUCH PING insulin pumps, Insulet Corporation's OMNIPOD system, Roche Insulin Delivery Systems Inc.'s ACCU-CHEK COMBO system, and Tandem Diabetes Care's TSLIM insulin pump. One example of a patch pump is described in U.S. Pat. No. 8,025,658 entitled "ADHESIVE PATCH SYSTEMS AND METHODS" issued on Sep. 27, 2011, which patent is hereby incorporated herein by reference in its entirety to the extent that it does not conflict with the present disclosure. Another example of an ambulatory infusion device is described in U.S. Patent Application entitled PERSONALIZED HOUSING FOR AMBULATORY INFUSION DEVICE, filed on the same day as the present application, having Ser. No. 14/063,870, and naming Michael Schmitz, Keith Hildebrand, Edwin Rivera and Dale Seeley as inventors, which patent application is hereby incorporated herein by reference in its entirety to the extent that it does not conflict with the disclosure presented herein. The devices and systems described above may be readily modified to employ refillable reservoirs described herein and may be used to deliver any suitable medicament for any suitable therapeutic purpose.

Ambulatory infusion devices require periodic movement of a cannula that is punctured through a patient's skin to avoid dermatological or immunological complications or infections. Often, the cannula is moved within three days or about every three days. In most ambulatory infusion devices, the drug path of the reservoir system includes the reservoir, fluid pathway and cannula that punctures the skin. If the drug runs out before the time period for movement of the cannula (e.g., three days), the reservoir, drug path and cannula may need to be replaced. However, with the infusion devices, systems and prefilled reservoir apparatuses described herein, the reservoir apparatuses may be replaced multiple times within the cannula life cycle (e.g., three days), which can present significant advantages to the patient.

With some ambulatory infusion devices, the reservoir may be removed, refilled, and reinserted without removing or replacing the infusion set or cannula. With such devices, embodiments of the prefilled reservoir apparatuses described herein provide for simpler drug replacement and avoid many of the complications or potential pitfalls with reservoir refilling.

In addition, the use of prefilled reservoir apparatuses as described herein may enable therapies that would be cumbersome or impractical with existing ambulatory infusion devices. For example, therapies that include one day delivery of one medicament followed by another one day delivery of another medicament may be readily accomplished with the infusion devices and prefillable reservoirs described herein. In situations where medicaments are incompatible, cannot be mixed, or are preferably not mixed or where sequential operations of medicament delivery can improve efficacy, minimize side effects, or the like, swapping of prefilled reservoir apparatuses containing the different medicaments may be readily accomplished with the devices, apparatuses and systems described herein. These and other advantages will be evident to those of skill in the art upon reading the following detailed description.

Figure 2:
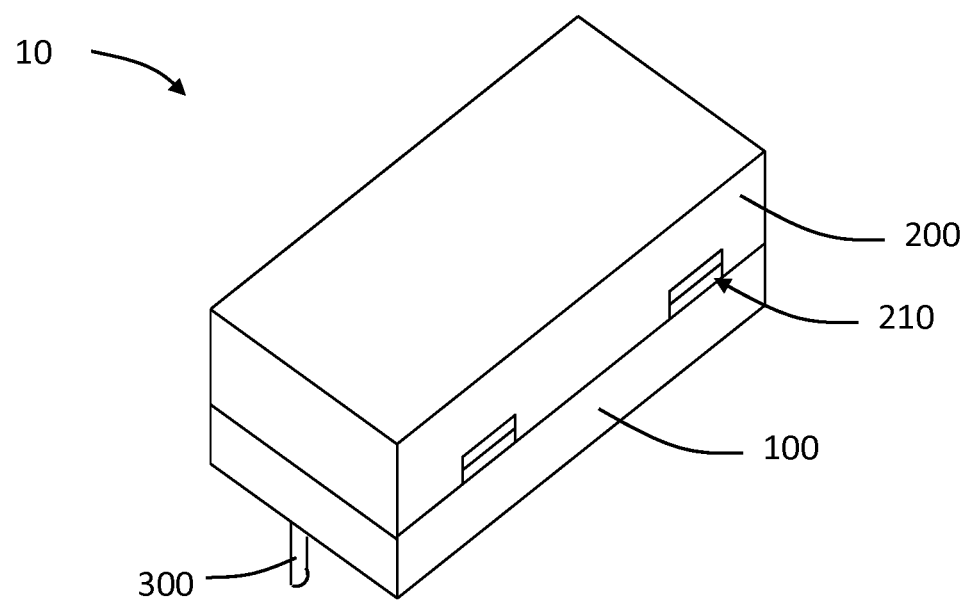

Referring now to FIGS. 1-2, schematic drawings of embodiments of ambulatory infusion devices 10 are shown. The infusion devices 10 include a base 100 and an upper unit 200. The base 100 and the upper unit 200 include cooperating engagement elements 210 to secure the base 100 relative to the upper unit 200. The infusion devices 10 include an outlet 300 for delivering a liquid composition comprising a medicament to the patient. In the embodiment depicted in FIG. 1, the outlet 300 comprises a tube or cannula for connection with an infusion set, which may, for example, be attached to a patient's skin. In the embodiment depicted in FIG. 2, the outlet 300 comprises a cannula for transcutaneously or subcutaneously delivering a liquid composition comprising a medicament to a patient, such as to a subcutaneous space of the patient. The infusion device 10 depicted in FIG. 2 may be a patch pump that would include an adhesive layer (not shown) between the base and the patient's skin for adhering the infusion device 10 to the patient.

In some embodiments, the upper unit 200 may function solely as a lid or cover. In some embodiments, the upper unit 200 may include a control unit having a processor or other control elements configured to control the rate at which the device 10 delivers a liquid composition comprising a medicament, as will be discussed in more detail below. In some embodiments, the upper unit 200 may be a rigid top of a reservoir apparatus.

Figure 3:
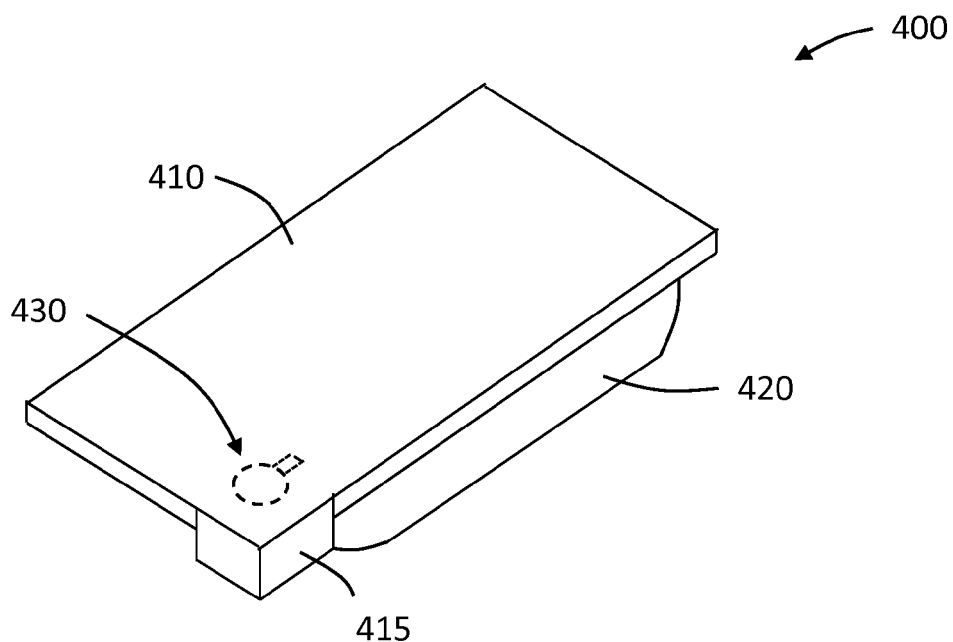
FIG. 3 is a schematic perspective view of an embodiment of a prefilled reservoir apparatus.

Referring now to FIG. 3, a schematic drawing of an embodiment of a reservoir apparatus 400 is shown. The reservoir apparatus 400 includes a rigid top 410 having an upper top surface and an opposing lower surface. The reservoir apparatus 400 includes a flexible bag 420 attached to the lower surface of the rigid top 410. The bag 420 may be attached to the top 410 by adhesive, welding, or the like. In embodiments, the lower surface of the rigid top 410 and the flexible bag 420 together form a reservoir for housing a liquid composition comprising a medicament. In embodiments, the bag 420 forms the reservoir for housing the liquid composition. The reservoir apparatus 400 includes a septum assembly 430 (shown in dashed lines as being under the upper surface of the top 410 in the depicted embodiment).

The septum assembly 430 comprises a tube in communication with the reservoir and a septum disposed in or about the tube. The septum is preferably a self-sealing septum, such as a silicone or rubber septum. The septum is positioned and configured to be pierced by a non-coring cannula of the base when the top 410 is received by the base. The septum is configured to seal about the cannula to prevent flow of the liquid composition from the reservoir through the septum around the cannula and to allow flow of the liquid composition from the reservoir to a lumen of the cannula.

In embodiments, the septum assembly 430 is attached to the rigid top 410. The septum assembly 430 may be attached to the top 410 in any suitable manner. In embodiments, the septum assembly 430 is molded into or inserted into a molded portion 415 of the top 410.

The rigid top 410 may be formed of any suitable material. Examples of suitable materials include metals, alloys, and polymers. Examples of suitable polymers include polycarbonate, TOPAS® COO cyclic olefin copolymers (TOPAS® is a registered trademark of Topas Advanced Polymers of Frankfurt-Höchst, Germany), polyetheretherketone (PEEK), high density polyethylene, polyurethane, polystyrene and the like. The rigid top 410 may be of any suitable thickness. Preferably, the top 410 is sufficiently thick to maintain structural integrity during handling, shipping, and manipulation. By way of example, the top 410 may have a thickness of between about 2 millimeters and about 4 millimeters. The top 410 may be of any sufficient rigidity to maintain its shape and stiffness during routine handling. By way of example, the top 410 may have a modulus of elasticity of about 3 GPa or greater.

In embodiments, the rigid top 410 is transparent or includes a transparent portion or window to allow visual inspection of the contents of the reservoir. This will allow inspection of color and clarity of the reservoir contents.

The flexible bag 420 may be formed of any suitable material. For example, the bag 420 may be formed from a thin polymeric film or sheet or a thin metal foil or sheet. Examples of suitable polymeric materials for forming thin polymeric sheets include polyvinylchloride (PVC), polyolefin, ethylene vinyl acetate, polypropylene, copolyester ether, and the like. Examples of thin metal sheets or foils that may be used include titanium or tantalum sheets or other metals with similar strain properties. High performance metals with high strain capability's (2%-8%) can are also be employed for additional security gains against cracking. This may be useful in such cases where the bag form factor requires more sever deformations. However, a thin metal sheet such as a foil may undue sever deformations to collapse as desired. Because the deformation is a one time deformation, typically cracking from cycling of such deformations should not be experienced. The bag 420 may include a coating or metalized layer to reduce permeation, to provide drug compatibility, or the like. By way of example, the bag 420 may include a metalized layer of aluminum. The bag 420 may be of any suitable thickness. By way of example, the bag 420 may have a thickness of between about 0.03 millimeters and about 1 millimeter. Preferably, the bag 420 is sufficiently flexible to avoid vacuum formation during removal of a liquid composition from a reservoir, which is formed at least in part by the bag 420, by a pump mechanism. By way of example, the bag 420 may have a modulus of elasticity of about 2 GPa or less.

In embodiments, the bag, or a portion thereof, 420 is transparent or includes a transparent portion or window to allow visual inspection of the contents of the reservoir.

Figure 4:
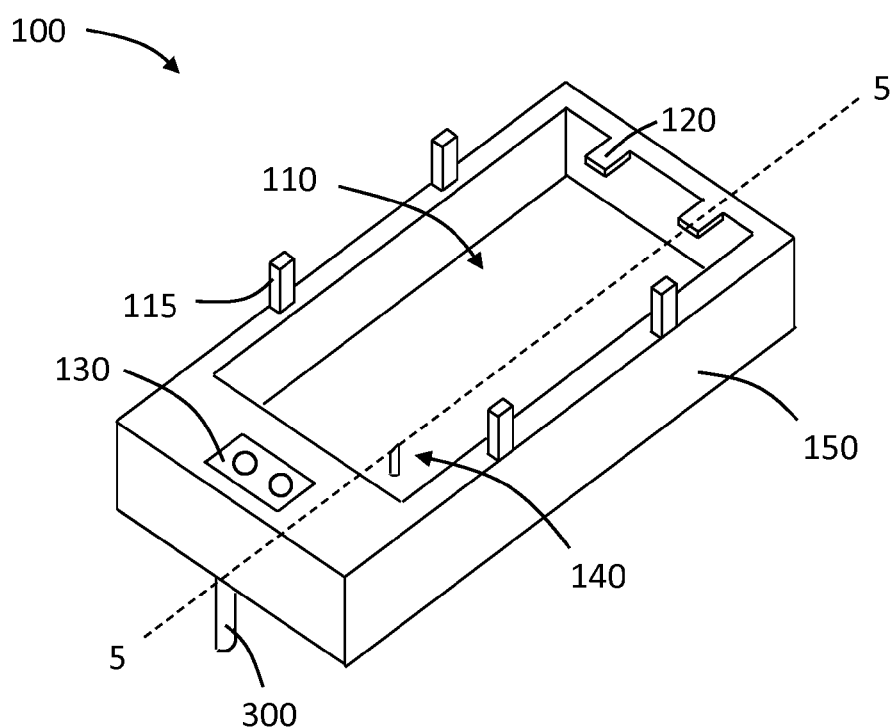
FIG. 4 is a schematic perspective view of an embodiment of a base of an ambulatory infusion device.

Referring now to FIG. 4, a schematic drawing of an embodiment of a base 100 is shown. The base 100 is configured to receive the reservoir apparatus. In the depicted embodiment, the base 100 has a housing 150 defining a cavity 110 configured to receive the reservoir apparatus or a portion thereof. The base 100 may also include one or more securing elements 115 for securing the base 100 relative to an upper unit, which as discussed above may be a lid or cover, a control unit or the reservoir apparatus. If the upper unit is the reservoir apparatus, the reservoir apparatus would have one or more corresponding securing elements to cooperate with the one or more securing elements 115 of base to secure the reservoir apparatus. In the embodiment, depicted in FIG. 4, the base 100 is configured to receive the reservoir apparatus in the cavity 110 and to cooperate with an upper unit that is a control unit. The base 100 includes an interconnect 130 for electrically coupling components of the base, such as a pumping mechanism, with components of the control unit.

In the embodiment depicted in FIG. 4, the base 100 includes features 120, such as tabs, extending over a portion of the cavity 110. The features 120 are configured to cooperate with the rigid top of a reservoir apparatus to facilitate retention of the reservoir apparatus within the cavity 110; e.g., as described below with regard to FIG. 5.

In the depicted embodiment, the base 100 also includes a non-coring cannula 140 having a lumen in communication with a fluid flow path of a pump mechanism (not shown in FIG. 4). The cannula is positioned such that the cannula punctures a septum of a reservoir apparatus in a non-coring manner when the reservoir apparatus is received by the base 100, thereby placing a reservoir of the reservoir apparatus in communication with the cannula and thus the fluid flow path of the pumping mechanism. The base 100 further includes an outlet cannula 300 in communication with the fluid flow path of the pumping mechanism.

The housing 150 of the base 100 may be formed from any suitable material, such as a metal, alloy, or polymeric material. In embodiments, the housing 150 is formed from a polymeric material. Examples of suitable polymeric materials include polycarbonate, TOPAS® COO cyclic olefin copolymers, polyetheretherketone (PEEK), high density polyethylene, polyurethane and the like.

Figure 5:
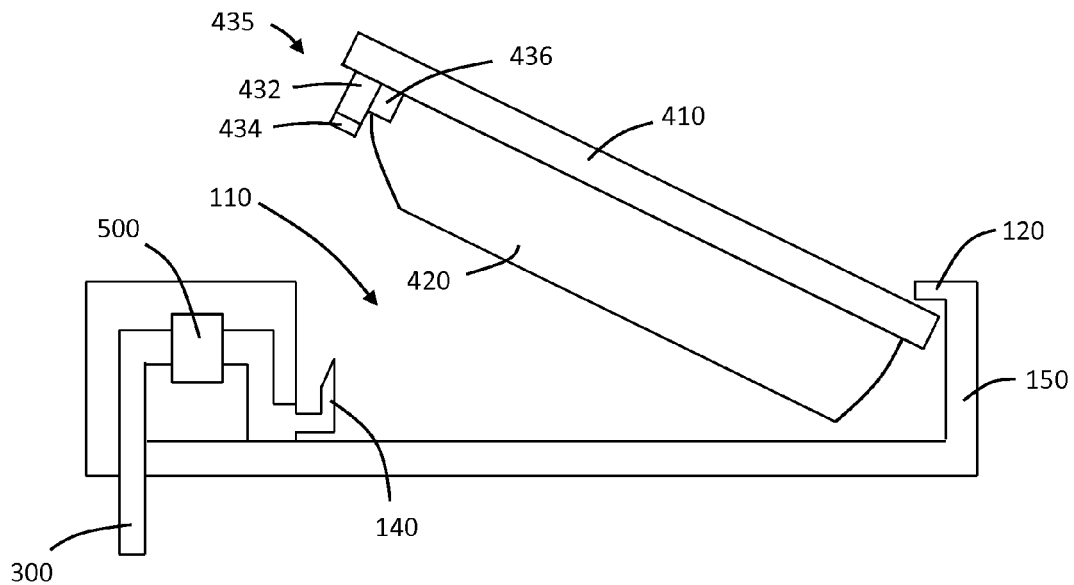
FIGS. 5-6 are schematic cross sectional views of embodiments of prefilled reservoir apparatuses and associated bases.

Referring now to FIG. 5, a schematic cross-sectional drawing of a base and reservoir apparatus is shown. The base depicted in FIG. 5 is an embodiment of the base 100 depicted in FIG. 4 with the section taken through line 5-5. As depicted, the cavity 110 of the base is configured to receive the receiver apparatus, with the top 410 and bag 420 configured to be retained in the cavity 110. Feature 120 of base that extends over cavity 110 has a top surface and an opposing bottom surface. The bottom surface of feature 120 is configured to engage with top surface of rigid top 410 of reservoir apparatus when the top 410 is received by the base.

When the reservoir apparatus is received by the base, the non-coring cannula 140 of the base is configured to pierce septum 434 that is sealingly disposed in or over a fluid flow path (a lumen of tube 432 in the depicted embodiment) that is in communication with a reservoir formed at least in part by bag 420 (via a lumen of tube 436 in the depicted embodiment). It will be understood that any suitable fluid flow path from septum assembly to reservoir may be employed. For example, a single tube may be employed, a fluid pathway through the housing may be employed, etc. The base includes a pump mechanism 500 having a fluid flow path in communication with a lumen of cannula 140 and outlet 300. Thus, when the reservoir apparatus is received by the base, the pump mechanism 500 is in fluid communication with the reservoir and may drive liquid composition from the reservoir via the lumen of cannula 140 to outlet 300.

Figure 6:
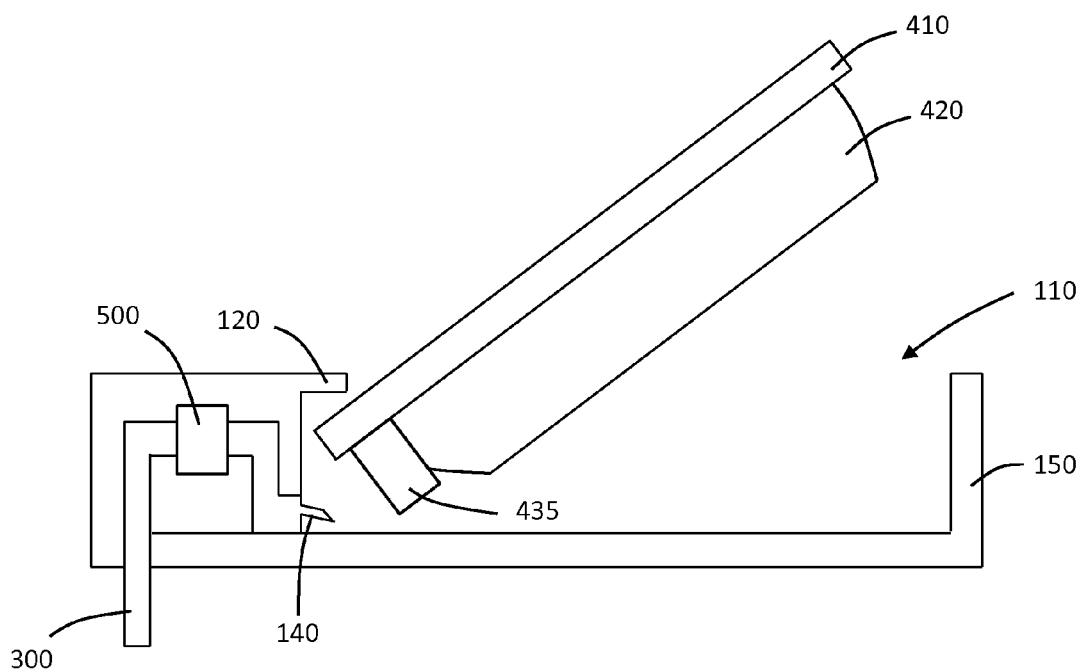

Referring now to FIG. 6, a schematic drawing of a cross-section of an alternative embodiment of base and reservoir apparatus is shown, where the non-coring cannula 140 of the base is positioned at a different angle relative to floor of the cavity 110. Many of the components of the reservoir assembly and base are the same or similar to those described above with regard to FIG. 5. To the extent specific components are not discussed with regard to FIG. 6, reference is made to the discussion above with regard to FIG. 5.

As shown in FIG. 6, the septum assembly 435 of the reservoir apparatus is correspondingly changed to accommodate the different angle of the non-coring cannula 140 (relative to the angle depicted in FIG. 5). In addition, the angle at which, and the manner in which, the reservoir apparatus is inserted into (or removed from) is altered to accommodate the changed angle of the cannula 140. The position or nature of securing feature 120 of base may also be changed to accommodate the change in angle of cannula 140 or the manner in which reservoir assembly is inserted into or removed from the cavity 110 of the base (e.g., as depicted in FIG. 6). Of course, any suitable securing or retention element may be employed to retain the reservoir assembly relative to the base.

In embodiments (not shown), the reservoir apparatus includes a non-coring cannula and the base includes a septum assembly configured to be pierced by the cannula of the reservoir assembly when the reservoir assembly is inserted into the base.

Figure 7:
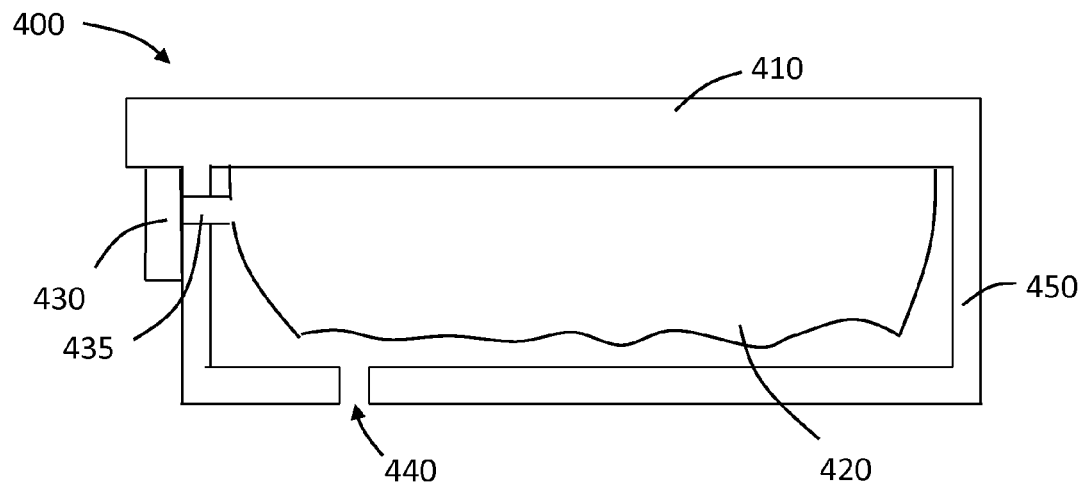
FIGS. 7-8 are schematic cross sectional views of embodiments of prefilled reservoir apparatuses having rigid housings.
Figure 8:
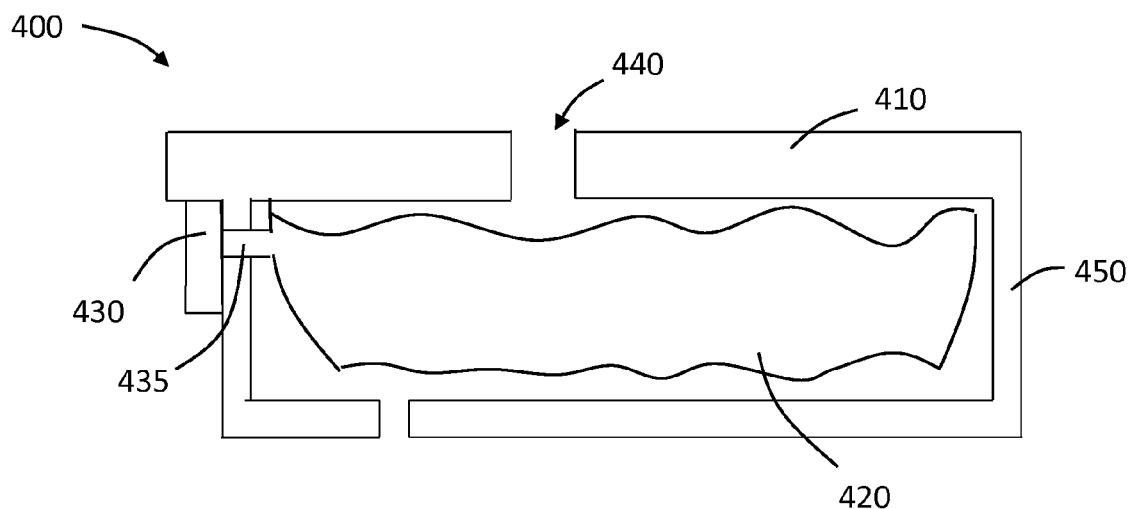

Referring now to FIGS. 7-8, schematic drawings of cross-sectional views alternative embodiments of reservoir apparatuses 400 are shown. In the depicted reservoir apparatuses, the rigid top 410 is a part of a rigid housing 450 in which the flexible bag 420 is disposed. The housing 450 may be formed of the same material as the rigid top 410 and may be of similar thickness and rigidity as rigid top 410. In the embodiment depicted in FIG. 7, the bag 420 and the lower surface of the rigid top 410 together form a reservoir for containing a liquid composition comprising a medicament. In FIG. 8, the bag 420 forms the reservoir. In both depicted embodiments, a lumen of a tube of septum assembly 430 is in communication with the reservoir. In addition, in both depicted embodiments, openings 440 are formed across the housing 450 to provide venting and collapse of bag 420 to reduce the likelihood of vacuum formation when liquid composition is pumped from the reservoir formed at least in part by the bag 420.

The reservoir apparatuses 400 depicted in FIGS. 7-8 are configured to be received by a base; e.g., in a manner similar to how reservoir apparatuses in FIGS. 5-6 were received by the based depicted in FIGS. 5-6.

In embodiments, the housing 450 is transparent or includes a transparent portion or window to allow visual inspection of the contents of the reservoir.

Figure 9:
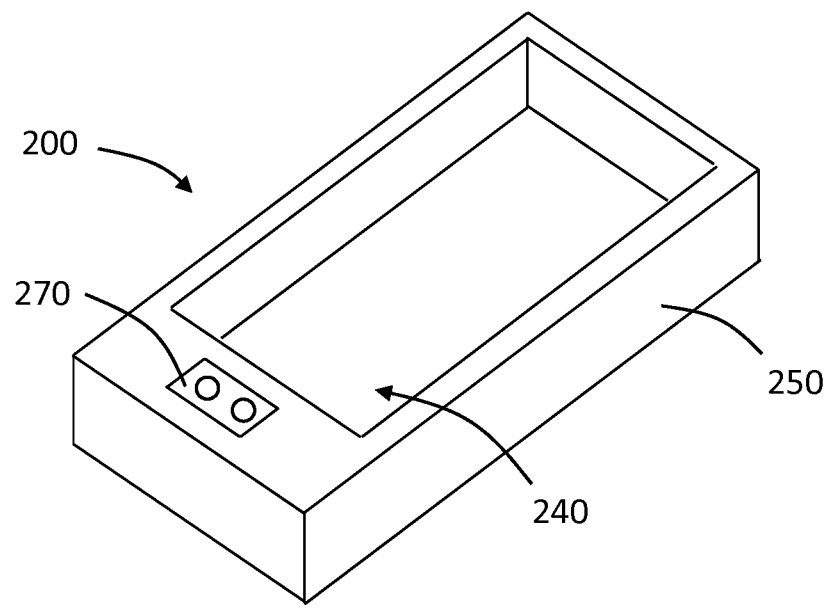
FIG. 9 is a schematic perspective view of an embodiment of a prefilled reservoir apparatus and a top portion of an infusion device.
Figure 9:
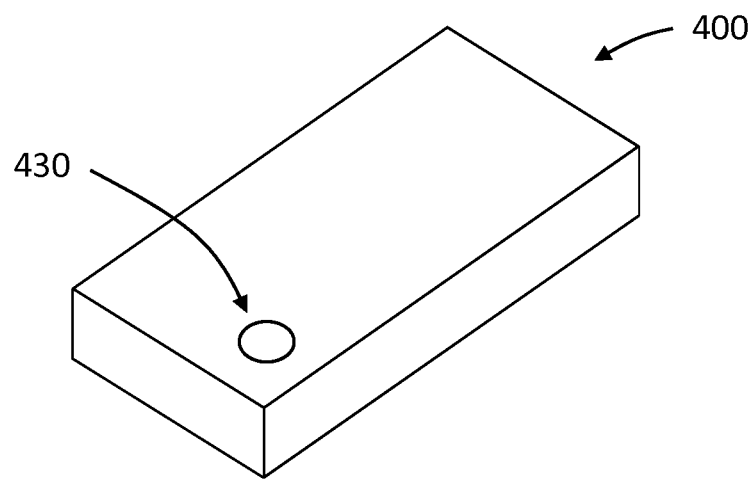

Referring now to FIG. 9, a prefilled reservoir apparatus 400 and an upper unit 200 of an infusion device or system are shown. The upper unit 200 may be the same or similar to an upper unit 200 depicted and described above with regard to FIGS. 1-2. The depicted upper unit 200 includes a housing 250 defining a cavity 240 configured to receive at least a portion of the reservoir apparatus 400. When the reservoir apparatus 400 is received by the upper unit 200, septum assembly 430 of the reservoir apparatus 400 is positioned such that when the upper unit 200 is operably secured relative to a base, a septum of the septum assembly 430 is pierced by a non-coring cannula having a lumen in communication with a pump. The upper unit 200 may include one or more features (not shown) for securing or retaining the reservoir apparatus 400, such as features 120 of base 100 depicted in FIGS. 4-6. As depicted in FIG. 9, the upper unit 200 may include an interconnect 270 for electrically connecting components (not shown) of the upper unit to a base (e.g., via interconnect 130 of base 100 depicted in FIG. 4).

Various embodiments of bases, reservoir apparatuses and upper units have been described above. However, other embodiments are contemplated. For example, in embodiments, the base may further include a power source and control electronics such as a processor, memory, or the like. In such embodiments, the upper unit may serve merely as a cover or lid or may be the rigid top of the reservoir apparatus. In such embodiments, an interconnect (e.g., interconnect 130 as shown in FIG. 4) may be omitted from base. In some embodiments, the upper unit serves as a control unit and contains control electronics, such as a processor, memory, or the like, to control the rate at which the pump mechanism in the base drives fluid from the reservoir of the reservoir apparatus to the outlet of the base. In such embodiments, the upper unit may further include a power supply. In some embodiments, the upper unit contains a power unit and the base includes control electronics or a power supply. Of course other configurations are possible and contemplated herein.

By way of example, an infusion device or system may be assembled from more than two, more than three, more than four, etc. units. The reservoir assembly may be inserted into a side (rather than top or bottom) of a unit. The reservoir assembly may include components other than a bag and a top or housing, such as electrical components, injection set components, or the like. The reservoir assembly may be inserted, at least partially, into a durable or consumable unit of the infusion device or system. The durable or consumable unit may be the base or upper unit described above or any other unit that, when assembled, forms a part of the infusion device or system.

Regardless of the configuration of the reservoir apparatus, a label (not shown) having information regarding drug content may be affixed to one or more of the bag, rigid top, or housing of the reservoir apparatus.

Figure 10A:
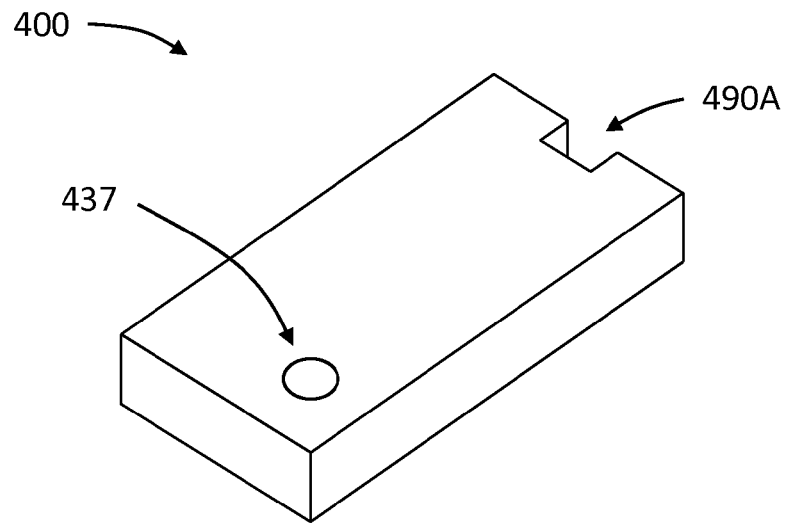
FIGS. 10A-B are schematic perspective views of embodiments of reservoir apparatuses having alignment features.
Figure 10B:
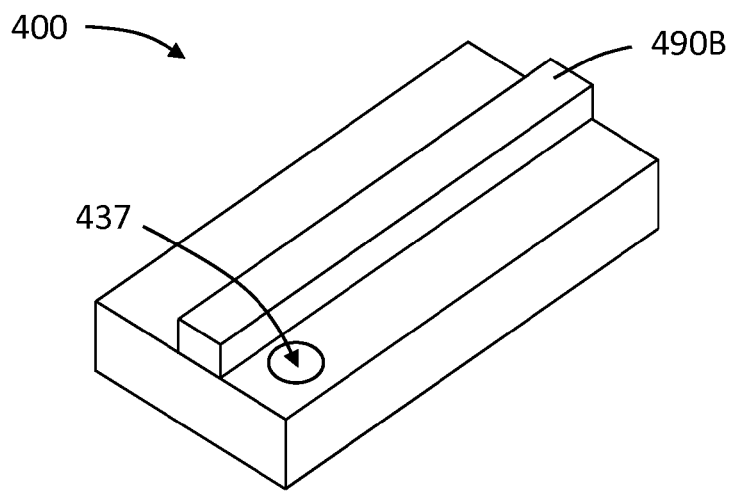

Referring now to FIGS. 10A-B, reservoir apparatus 400 may include one or more alignment features 490A, 490B configured to assist alignment of reservoir apparatus 400 during a filling procedure, such as an inline filling procedure at a manufacturing facility. The alignment features 490A, 490B may be formed in or on, or attached to, any suitable part of the reservoir apparatus 400, such as rigid top 410 or housing 450 described above. The alignment features 490A, 490B may also serve to align the reservoir apparatus with the infusion device or unit thereof. Alignment features may include an indent 490A, detent 490B, geometrical differences across a portion of the apparatus, height changes, ridges, vertical or depressed landmarks, flanges, embossments, or the like.

For purposes of aseptic filling, reservoir apparatus 400 preferably includes a septum assembly 437 in communication with the interior of bag (not shown in FIGS. 10A-B). The septum assembly 437 for filling may be the same as the septum assembly (e.g., septum assembly 435 depicted in, and described with regard to, FIGS. 5-6 above) for delivery by the infusion device. Of course, the reservoir assembly 400 may include a separate septum assembly 437 for filling the reservoir and a separate septum assembly for delivery via an infusion device.

A filling apparatus may include features that are complementary to the alignment feature 490A, 490B of the reservoir apparatus 400. The alignment features 490A, 490B of the reservoir apparatus 400 and complementary features of the filling machine may cooperate to align a cannula of the filling apparatus with a septum of the septum assembly 430 for filling the reservoir.

The methods, systems and devices described herein may be used to deliver any suitable therapy to a patient. Any suitable liquid composition comprising any suitable medicament may be delivered to a patient through use of infusion devices described herein. In embodiments, a prefilled reservoir apparatus is filled with an injectable composition. The injectable ropinirole composition may be an isotonic, citrate-buffered (pH about 4.5), injectable solution that contains 15 mg/ml ropinirole hydrochloride The reservoir apparatuses are preferably prefilled with liquid composition comprising medicament and terminally sterilized with the drug product prior to shipment for use in an infusion device assembly. However, the reservoir apparatuses may be prefilled by aseptic technique without further sterilization. In embodiments, the reservoir apparatuses are filled by a healthcare provider such as a pharmacist or physician. Of course, the reservoir apparatuses may be filled by a patient who has developed a level of comfort and expertise to fill the apparatus with liquid composition comprising medicament. Regardless of who fills the reservoirs of the reservoir apparatuses, the apparatuses may be filled by injecting a liquid composition across the septum into the reservoir.

As used herein, "filling" or the like, in the context of a reservoir, means introducing fluid into a reservoir. While "filling" encompasses filling to full capacity, "filling" also includes adding amounts of fluid that do not result in a full status of the reservoir.

Thus, embodiments of PREFILLED RESERVOIR APPARATUS FOR AMBULATORY INFUSION DEVICE are disclosed. One skilled in the art will appreciate that the apparatuses, systems and methods described herein can be practiced with embodiments other than those disclosed. The disclosed embodiments are presented for purposes of illustration and not limitation. One will also understand that components of the prefilled reservoirs and associated devices and systems depicted and described with regard the figures and embodiments herein may be interchangeable.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, apparatus, system, method or the like, means that the components of the composition, apparatus, system, method or the like are limited to the enumerated components and any other components that do not materially affect the basic and novel characteristic(s) of the composition, apparatus, system, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

The invention claimed is:

1. A prefilled reservoir apparatus for a medical infusion device, comprising:
    a rigid top having an upper surface and an opposing lower surface, the top being configured to be received by a base of a medical infusion apparatus;
    a flexible bag forming at least a portion of a reservoir, the bag being attached to the lower surface of the rigid top;
    a liquid composition comprising a medicament, wherein the liquid composition is disposed within the reservoir; and
    a septum assembly comprising a fluid flow path in communication with the reservoir and a self-sealing septum disposed in or over the fluid flow path, the septum being positioned and configured to be pierced by a non-coring cannula of the base as a result of coupling the top and the base, wherein the septum is configured to seal about the cannula to prevent flow of the liquid composition from the reservoir through the septum around the cannula and to allow flow of the liquid composition from the reservoir to a lumen of the cannula.

2. The prefilled reservoir apparatus of claim 1, wherein the lower surface of the rigid top and interior of the bag form the reservoir.

3. The prefilled reservoir apparatus of claim 1, wherein the rigid top is part of a rigid housing in which the bag is disposed.

4. The prefilled reservoir apparatus of claim 1, wherein the liquid composition is a sterile liquid composition.

5. The prefilled reservoir apparatus of claim 4, wherein the liquid composition comprises ropinirole and has a pH of 4.5.

6. A system comprising:
    the prefilled reservoir apparatus of claim 1; and
    the base.

7. The system of claim 6, wherein the base comprises a cavity for receiving the flexible bag.

8. The system of claim 7, wherein the base further comprises a feature extending over a portion of the cavity, the feature having a top surface and an opposing bottom surface, wherein the bottom surface of the feature is configured to engage the top surface of the rigid top of the reservoir apparatus when the top is received by the base.

9. The system of claim 6, wherein the base comprises a pump mechanism in communication with the lumen of the cannula, the pump mechanism configured to drive the liquid composition from the reservoir via the lumen of the cannula to an outlet.

10. The system of claim 9, wherein the base further comprises an electrical interconnect configured to electrically couple with an interconnect of a control module, wherein the pump mechanism is electrically coupled to the interconnect of the base.

11. The system of claim 10, further comprising the control module.

12. The system of claim 11, wherein the control module comprises control electronics electrically coupled to the interconnect of the control module, wherein the control electronics are configured to control the rate at which the pump mechanism drives the liquid composition from the reservoir.

13. A prefilled reservoir apparatus for a medical infusion device, comprising:
 a rigid housing configured to be received by a base of a medical infusion apparatus;
 a flexible bag forming a reservoir and disposed in the housing;
 a liquid composition comprising a medicament, wherein the liquid composition is disposed within the reservoir; and
 a septum assembly comprising a fluid flow path in communication with the reservoir and a self-sealing septum disposed in or over the fluid flow path, the septum being positioned and configured to be pierced by a non-coring cannula of the base as a result coupling the housing and the base, wherein the septum is configured to seal about the cannula to prevent flow of the liquid composition from the reservoir through the septum around the cannula and to allow flow of the liquid composition from the reservoir to a lumen of the cannula.

14. The prefilled reservoir apparatus of claim 13, wherein the liquid composition is a sterile liquid composition.

15. A system comprising:
 the prefilled reservoir apparatus of claim 13; and
 the base.

16. The system of claim 15, wherein the base comprises a cavity for receiving the housing of the reservoir apparatus.

17. The system of claim 15, wherein the base comprises a pump mechanism in communication with the lumen of the cannula, the pump mechanism configured to drive the liquid composition from the reservoir via the lumen of the cannula to an outlet.

18. The system of claim 17, wherein the base further comprises an electrical interconnect configured to electrically couple with an interconnect of a control module, wherein the pump mechanism is electrically coupled to the interconnect of the base.

19. The system of claim 18, further comprising the control module.

20. The system of claim 19, wherein the control module comprises control electronics electrically coupled to the interconnect of the control module, wherein the control electronics are configured to control the rate at which the pump mechanism drives the liquid composition from the reservoir.

* * * * *